(12) United States Patent
Lehmann

(10) Patent No.: US 6,787,331 B2
(45) Date of Patent: Sep. 7, 2004

(54) PROCESS FOR EXAMINING MEMBRANE ENCLOSED BIOCOMPARTMENTS

(75) Inventor: Mirko Lehmann, Freiburg (DE)

(73) Assignee: Micronas GmbH, Freiburg (DE)

(*) Notice: Subject to any disclaimer, the term of this patent is extended or adjusted under 35 U.S.C. 154(b) by 349 days.

(21) Appl. No.: 09/875,220

(22) Filed: Jun. 6, 2001

(65) Prior Publication Data

US 2002/0028478 A1 Mar. 7, 2002

(30) Foreign Application Priority Data

Jun. 9, 2000 (DE) .......................... 100 28 692

(51) Int. Cl.⁷ ................................ C12Q 1/02
(52) U.S. Cl. .................. 435/29; 435/34; 204/403.01
(58) Field of Search .................. 435/29, 34, 431, 435/817; 204/403.01; 205/777.5

(56) References Cited

U.S. PATENT DOCUMENTS

| | | | | |
|---|---|---|---|---|
| 5,037,737 | A | * 8/1991 | Liffmann et al. | 435/11 |
| 5,376,255 | A | 12/1994 | Gumbrecht et al. | |
| 5,851,489 | A | 12/1998 | Wolf et al. | |
| 6,153,069 | A | * 11/2000 | Pottgen et al. | 204/403.11 |
| 6,297,025 | B1 | * 10/2001 | Sugihara et al. | 435/29 |

FOREIGN PATENT DOCUMENTS

| | | |
|---|---|---|
| DE | 3806955 C2 | 6/1990 |
| DE | 4401839a1 | 7/1995 |
| DE | 4438087 A1 | 5/1996 |
| DE | 4417079 C2 | 6/1998 |
| DE | 19753598 C1 | 7/1999 |
| EP | 0 870 823 A1 * | 10/1998 |

OTHER PUBLICATIONS

Lehmann M. Non–Invasive Measurement of Cell Membrane Associated Proton Gradients by Ion–Sensitive Field Effect Transistor Arrays for Microphysiologicol and Bioelectronical Applications. Biosensors & Bioelectronics 15(3–4)117–124, 2000.*

Rybak S. Theoretical Considerations on the Role of Membrane Potential in the Regulation of Endosomal pH. Biophysical J 73(2)674–687, 1997.*

Al–Baldawi N. Calcium Accumulation by Organelles Within Myxicola Axoplasm. J of Physiology 461:633–646, Feb. 1993.*

* cited by examiner

Primary Examiner—Ralph Gitomer
(74) Attorney, Agent, or Firm—Volpe and Koenig P.C.

(57) ABSTRACT

A process for the examination of biocompartments (1), having a micro-flow chamber (2) which contains a biocompartment (1) which is continually or intermittently subjected to the through-flow of a culture medium. In a culture medium zone proximal to the biocompartments (1), an electrical potential is applied in such a manner, that from a substance in the culture medium which is released or consumed by the biocompartments (1), OH⁻ and/or H⁺ ions are formed. During the application of the potential, a first measurement ($pH_{-1}$, $pH_{-3}$) for the pH value of the culture medium is measured. The potential is then switched off or changed in such a manner that the formation of OH⁻0 and/or H⁺ ions from the said substance is stopped. Before or after the measuring of the first measured value, ($pH_{-1}$, $pH_{-3}$) with switched off electrical potential, a second measured value ($pH_{-2}$, $pH_{-4}$) is measured for the pH value of the culture medium. After the entire measurement is repeated at least once, then from the first and second measurement values, the concentration change of the substance in the culture medium and the acidification or alkalinization of the culture medium is determined.

10 Claims, 5 Drawing Sheets

PROCESS FOR EXAMINING MEMBRANE ENCLOSED BIOCOMPARTMENTS

BACKGROUND

Figure 1:
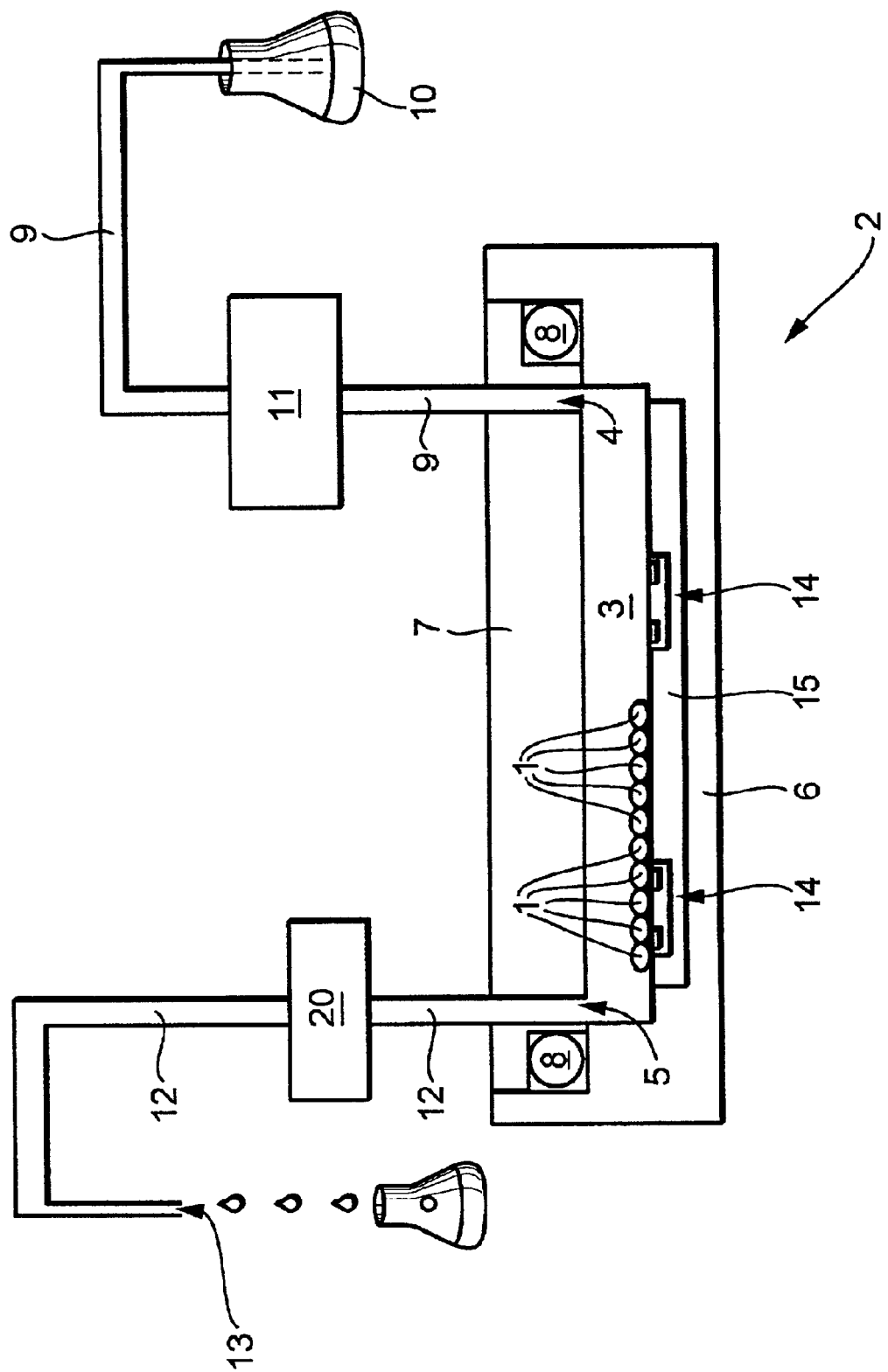

This application claims priority to German Application No. 100 28692.5 filed Jun. 9, 2000.

The invention concerns a process for examining of membrane enclosed biocompartments, wherein the biocompartments are arranged in amicro-flow chamber. This micro-flow chamber is subject to the through-flow of a culture medium containing an active agent and which is in contact with the said biocompartments and possibly has an effect thereon. Further, the pH value of the culture medium present in the micro-flow chamber can be measured. In this arrangement, the biocompartments can hold, for instance, biological cells, microorganisms (fungi, bacteria), biochemical compartments and/or mitochondria.

EP 0 394 406 B1 discloses a process of the type known in the art, in which living, biological cells are placed in a micro-flow chamber being subjected to the through-flow of a culture medium and which chamber has a silicon sensor on its bottom. A reference electrode is provided in the micro-flow chamber, which is in continual contact with the culture medium. In the case of this previously known process, in a first process step, the through-flow of the culture medium is stopped in the micro-flow chamber. Under these circumstances, the pH value, serving as a metabolic indicator of substance change in the culture medium residing in the micro-flow chamber, is determined by measurement of the electrical potential between the silicon-sensor and a reference electrode. With this process, it is possible to measure, for instance, the action of a cell-affecting agent on the metabolism of the cells. A detriment, however, lies in the fact, that the process enables only one determination in regard to a yield of acid metabolic products, while other changes caused by the metabolism of the cells are not given consideration.

DE 44 17078 A1 makes known a process wherein biological cells in a micro-flow chamber are simultaneously examined by means of a plurality of different micro-sensors. As this is carried out, in addition to the acidification, at the same time the respiration of the cells in the culture medium is monitored, which enables a more exact investigation of the action on the cells of an agent contained in the culture medium. This procedure, however, has the disadvantage, that the measured values for pH and oxygen content are determined at different places and thus of differing biological cells present in the micro-flow chamber. Cell cultures, cell divisions, tissues and the like which are to undergo examination as biological material are, however, often heterogenous, that is, different cells can yield different signals. In this known procedure, on this account, imprecisions in the investigation of an agent in the culture medium can occur if the pH value and/or the oxygen content at the points of determination of the sensors deviate in pH and oxygen content from one another.

SUMMARY

Thus, it is the object of the invention, to make available a process for the examination of membrane enclosed biocompartments, which enables the measurement at one location of several metabolic parameters of the said biocompartments.

The achievement of this object is found especially in that:

a) the concentration of substance which is yielded or absorbed by metabolism in the micro-flow chamber in a partial increment of the culture medium in the active area of the biocompartments is indirectly measured, since between an operational electrode placed in said partial increment and a distanced reference electrode, an electrical potential is so applied to the culture medium, that hydroxyl or hydrogen ions are formed from substances in the culture medium, b) at a measuring point in the partial increment of the culture medium during the application of the said electrical voltage, at least one first value for a pH value of the culture medium is determined, c) subsequently, the electrical voltage will be turned off or changed in such a way, that the formation of hydroxyl ions and hydrogen ions from the said substance ceases, d) shortly before or after the measurement of the first value at shut-off voltage, or by a voltage in which the generation of hydroxyl and hydrogen ions from the said substance is not possible, at least a second measurement value is determined for the pH value of the culture medium, e) from the first and the second measured values, a difference is calculated, f) the steps a) to e) are repeated at least once, g) from a difference between at least two of these measured value differences, the concentration change of the material in the culture medium, and from the difference between at least two of the first pH measurements or the second pH values, the acidification or alkalinizations of the culture medium can be determined, h) and from the so obtained measurement values for the concentration change as well as the acidification or alkalinization, the metabolic activity of the biocompartments can be determined.

The basis of the process lies in the recognition, that the biocompartments continually change the pH value of the culture medium at a somewhat constant increase. Further, this alteration of pH value runs essentially slower than the pH change arising from an application of electrical voltage for the generation of hydroxyl ions ($OH^-$ ions) or hydrogen ions ($H^+$ ions) from substances in the culture medium yielded by, or absorbed by metabolism in the biocompartments. This contributes to the fact that it becomes possible in spite of the superimposing of the ions of hydroxyl and/or hydrogen yielded to or taken from the culture medium by the biocompartments with those ions of hydroxyl or hydrogen from substance carried in the culture medium, at one and the same location, and with only a single pH-sensor, to measure both the substance which arises from the concentration change activated by the biocompartments of the material yielded to or taken from the biocompartments as well as the pH change in the culture medium caused by the biocompartments. With the inventive process, it becomes possible to determine the respiration of the biocompartments by the measurement of the oxygen concentration change, as well as the concentration change of nitrogen monoxide (NO), hydrogen peroxide, and/or other compounds containing oxygen and/or hydrogen in a chemically bound form, such as, for instance, molecules which are present in the cell surfaces. A dependency of change of concentration and/or pH value based on localization caused by a difference in the individual cells of the cell culture has practically no effect on the accuracy of the determination of the metabolism of the cells undergoing examination.

From Sohn, B.-H., Kim, C.-S., "A new pH-ISFET-based dissolved oxygen sensor by employing electrolysis of oxygen" in *Sensors and Actuators* B34, (1996), pages 435–440, is, to be sure, an already disclosed process, contrary to the generic type, in which the oxygen content in analytes is measured indirectly by means of the pH value, wherein the electrical potential on the analyte is so far reduced in the negative direction, that from such oxygen as is in the analyte, hydroxyl ions are formed, and wherein these hydroxyl ions are detected by means of an ion selective sensor. The analyte contains, however, no biocompartments which change during the measurement, that is, which change the analyte by means of acid metabolic products and the consumption of oxygen. Also, this known procedure results in no evaluation of the sensor signal in regard to the determination of respirational activity and acidification when potential is not reduced.

In a particularly advantageous embodiment of the process, a provision is made that the sequence comprising the steps a) to g) is run through at least twice and that in these at least duplicated operations, the polarity is differently chosen between the electrical potential applied between the operational electrode and the reference electrode. This makes it possible to measure in the culture medium, using only one pH-value sensor, both the concentration change of electro-negative substances, such as oxygen, as well as the concentration of electro-positive substances, such as nitrogen monoxide or hydrogen peroxide.

With this arrangement, in the measurement of the change in concentration of an electro-negative substance, there is applied to the operational electrode, an electrical potential which is negative relative to the potential of the reference potential. Conversely, if the operational electrode is to measure the concentration change of an electro-positive substance, then the applied potential is to be, in the same manner, positive.

It is advantageous, if the time for the measurement of the pH-value is arranged to fall in such a manner on the time at which the electrical potential changes or is shut off, so that the ion concentrations of respectively hydrogen and hydroxyl at the measurement instant are essentially in equilibrium. The metabolism, that is, the viability of the biocompartments can be measured with greater precision with such timing.

In another advantageous embodiment of the invention, provision has been made, that respectively, the period, between the moment of the application, the shutting off, or changing of the electrical voltage, and the subsequent time at which a pH measurement is made, is essentially made the same for all pH values. In this way, in the forming of a difference between the first and second pH values upon the measurement of the concentration change in the culture medium by the material involved in the metabolic activity of the biocompartments that is, from a first pH value from the measurement of the change of pH value in the culture medium caused by the biocompartments, compensation is provided for what effect time may have in regard to the period between the beginning of a potential change and the subsequent measurement of the pH value. This contributes to an even greater accuracy in measurement.

It is of particular advantage, if the electrical voltage is cut off, or, in accord with step c) is changed, before a state of equilibrium has established itself in the hydrogen ion and the hydroxyl ion concentrations in the culture medium. The biocompartments in the micro-flow chamber are then only subjected for a short time to the application of the electrical potential required for the formation of the hydroxyl ions or hydrogen ions. Thus, the biocompartments remain substantially unaffected in their physiological condition by the application of potential.

This situation enables the carrying out of measurements on the biocompartments for a longer period. This provides the ability to successively bring more different agents in contact with the biocompartments and to compare their various activities on the biocompartments with one another.

In an advantageous embodiment of the process, the electrical current flowing between the operational electrode and the reference electrode is measured. The curve of the electrode current can then be compared with the curve of the electrical voltage applied to the electrodes, and if necessary, compared also with a previously stored Amp/Volt-characteristic line or with a family of such curves, which will provide another checkpoint in monitoring the plausibility of the results of the measurements.

Expediently, the biocompartments are so placed in reference to the operational electrode, that they—at least in an area sense—cover over the electrodes. From the time related curves of the electrical potential between the operational electrode and the reference electrode, along with that of the electrode current, a possible alteration of the morphology or adhesion of the biocompartments can be determined.

It is of particular advantage, if the pH value is measured by means of an Ion Selective Field Effect Transistor (hereinafter ISFET). Because of the capability of such a sensor to respond in a range of small signals, the inventive process is enabled to make a high degree of placement determination, whereby it is even possible to investigate single cells of the cell culture and to compare the thereby obtained measurements with each other. In this manner, for instance, in a cell culture, single cells which react especially sensitively to a given agent can be localized.

In another advantageous embodiment of the invention, the through-flow of the culture medium is stopped, or at least reduced, during and in between the taking of the first and last pH measured values of a provided series of pH value determinations for the establishing of the respiratory activity of the biocompartments and the pH value change activated by said biocompartments in the culture medium. The oxygen content diminishes during the time following the stopping or reducing of the culture medium through-flow in a case of oxygen consuming biocompartments.

Conversely, in the case of photosynthetic biocompartments which generate oxygen, the oxygen content will increase. In this situation, however, a correspondingly large measurement signal is produced, which makes possible an exact determination of the respiratory activity of the biocompartments. Where biocompartments are concerned which consume oxygen, after the stopping or reducing of the culture medium through-flow, an increase in the pH value of the culture medium occurs, and in the case of biocompartments, which produce oxygen, a decline in pH values is evident. In this way, there is available a correspondingly large measurement signal because of the pH value change of the culture medium activated by the biocompartments.

BRIEF DESCRIPTION OF THE DRAWING(S)

Figure 2:
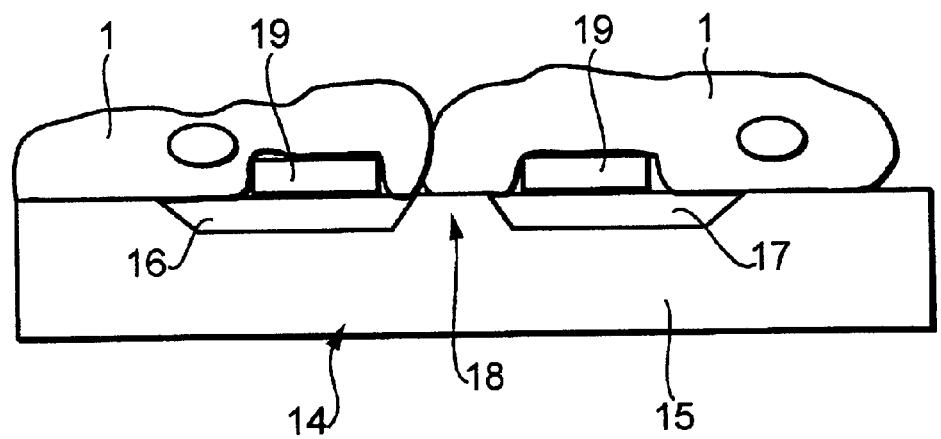
Figure 3:
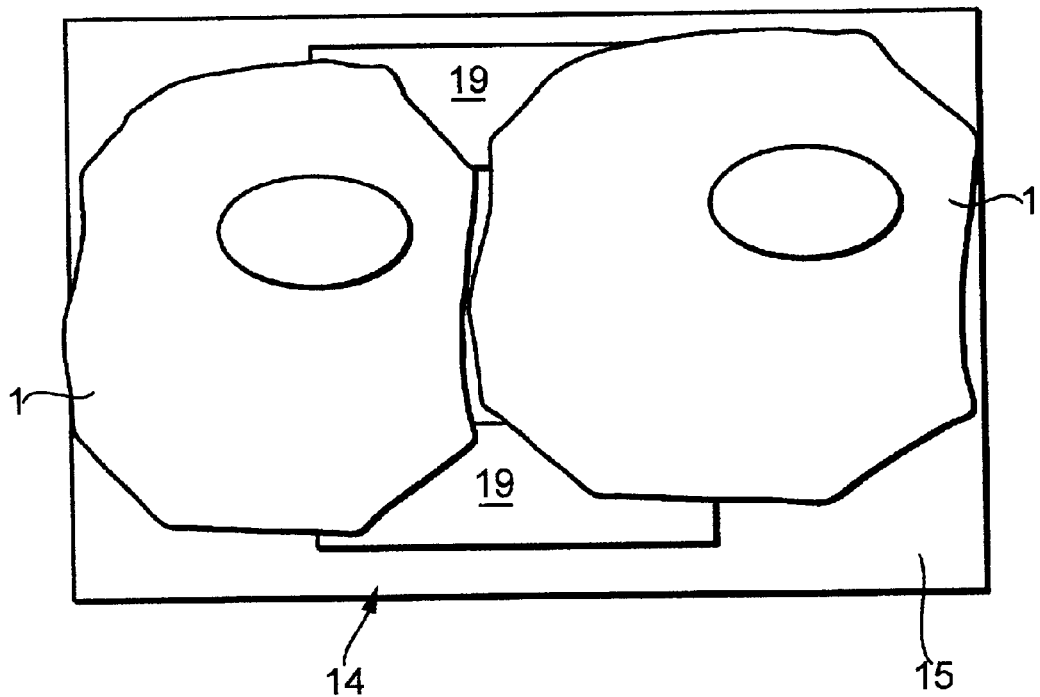
Figure 4:
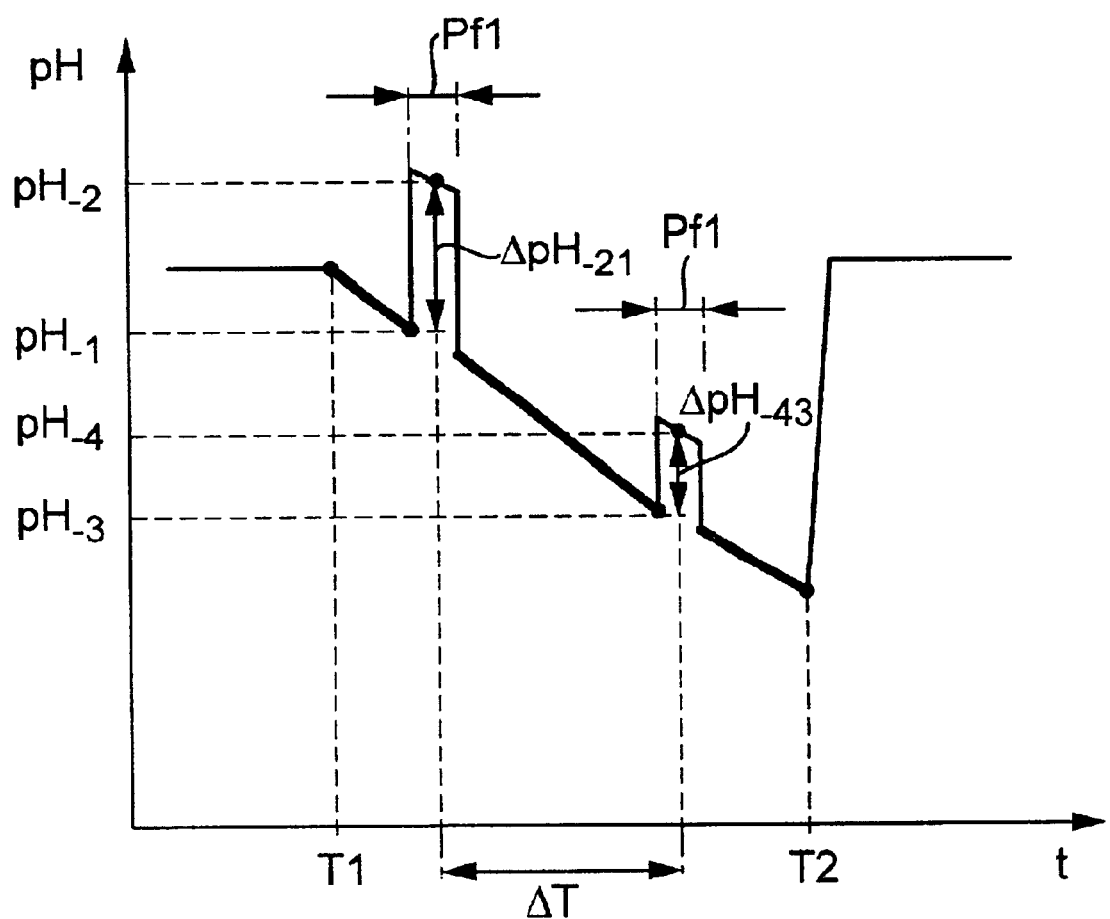
Figure 5:
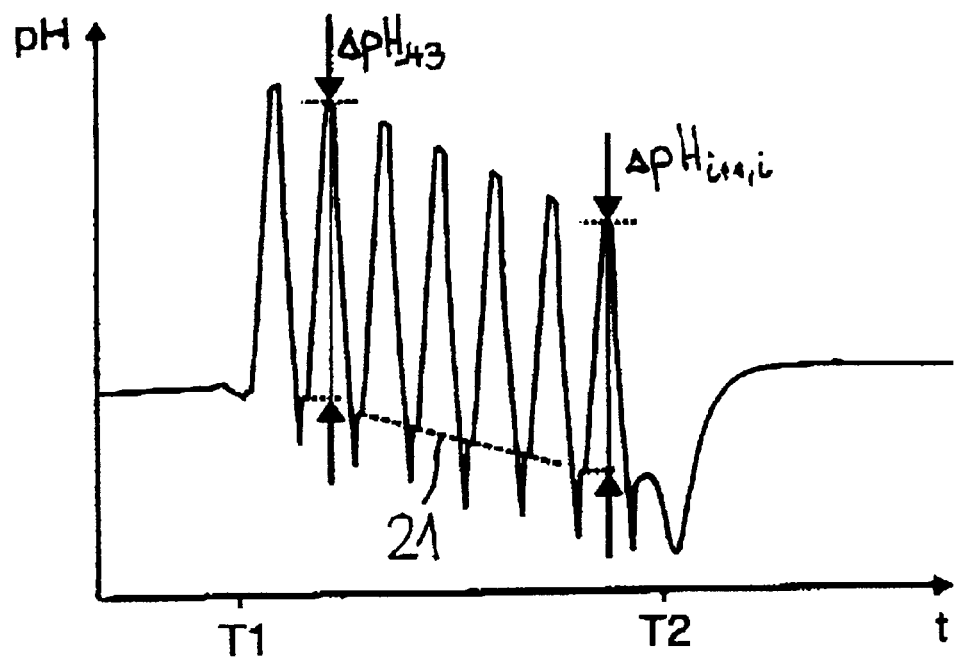
Figure 6:
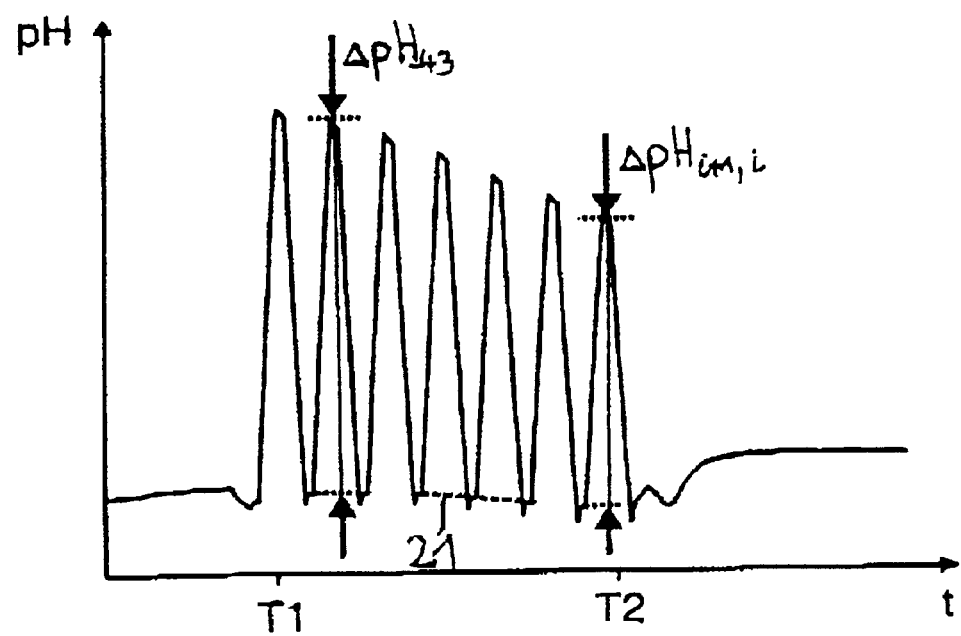
Figure 7:
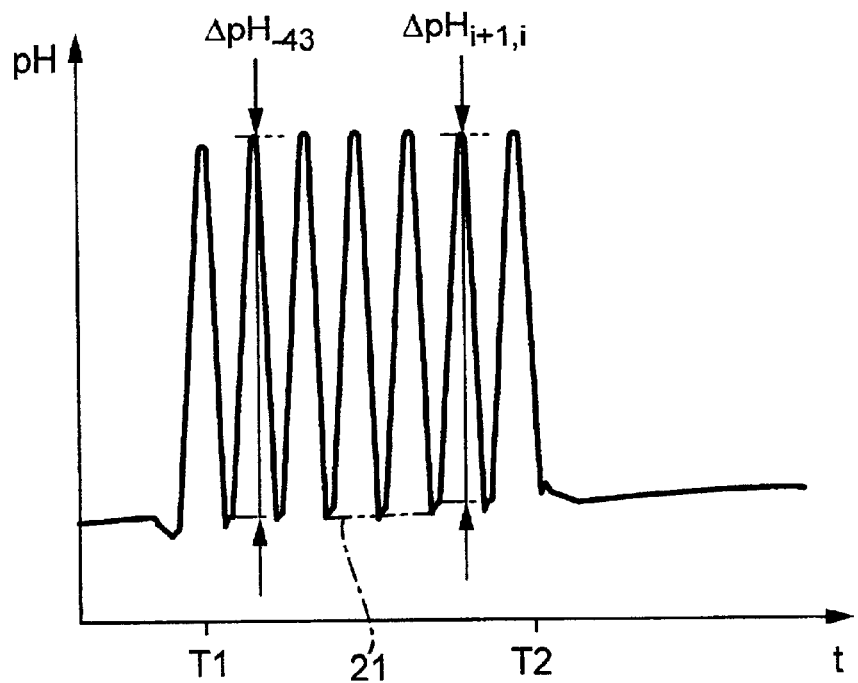
Figure 8:
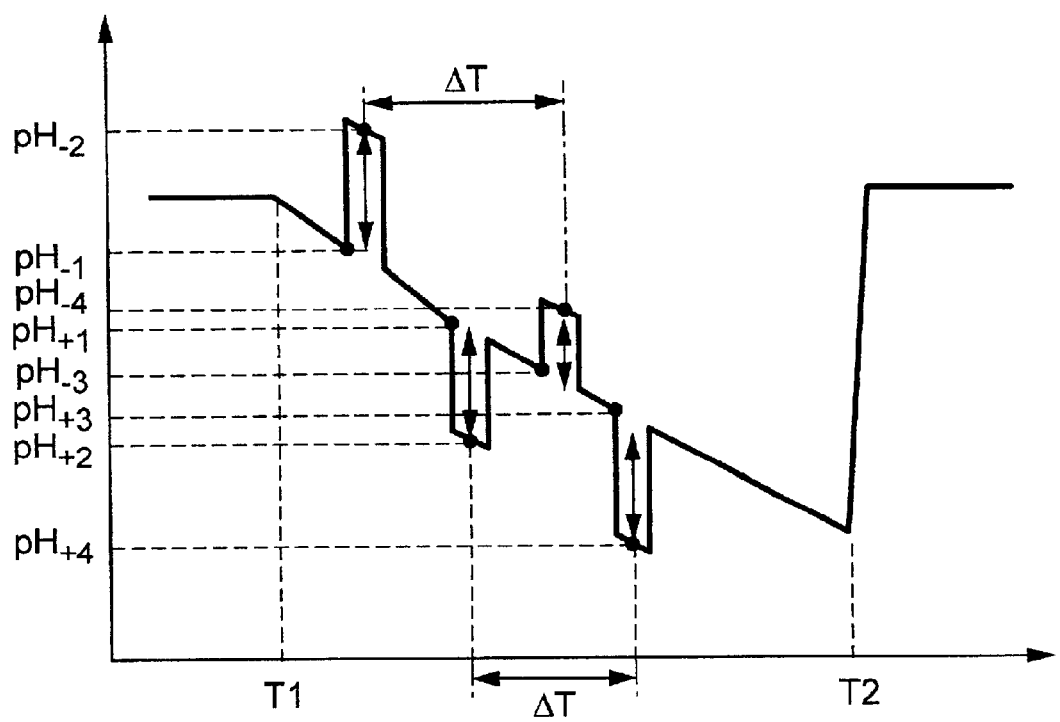

What follows is a detailed description of preferred embodiments of the invention, which described are in more detail with the aid of the drawings. Shown in a schematic manner are:

FIG. 1 is a longitudinal section through an apparatus with a micro-flow chamber for the examination of living, membrane enclosed, biocompartments, FIG. 2 is a longitudinal section through an ISFET inserted in the base of the micro-flow chamber with an electrode placed proximal to said ISFET, whereby, on the ISFET and on the electrode, biological cells are adherently placed, FIG. 3 is a plan view of the arrangement shown in FIG. 2, FIG. 4 is a graphical representation of a measurement signal obtained by an ISFET, wherein the measurement signal curve is depicted only schematically, FIG. 5 is a graphical representation of a determined measurement signal obtained by an ISFET in the micro-flow chamber, whereby on the abscissa, the time and on the ordinate scale, the pH value is depicted, and wherein the cell culture medium found in the micro-flow chamber is substantially free of cell-affecting agents, FIG. 6 is a representation similar to FIG. 5 whereby, however, iodine acetate is contained in the cell culture medium as a cell affecting agent, FIG. 7 is a representation similar to FIG. 5, whereby, however, in the cell culture medium, Tritone® is contained, and FIG. 8 is a representation similar to FIG. 4, whereby, however, at each application of an electrical potential onto the culture medium, the polarity of the potential was changed.

DETAILED DESCRIPTION OF THE PREFERRED EMBODIMENTS

In a process for the examining of membrane enclosed biocompartments, biocompartments 1 were designed as biological cells placed in amicro-flow chamber 2. The micro-flow chamber 2 possesses a measurement space 3, enclosed by a chamber housing. The space 3 is provided with an inlet opening 4 and an exit opening 5 for nutrient or culture medium. The chamber housing has a chamber base part 6 and a top part 7 which fits said base part 6 and the two parts are sealed liquid tight to one another by an interposed sealing ring 8.

The inlet opening 4 of the measurement space is connected to the measuring space 3 by a feed conduit 9, which in turn is connected to a culture medium supply 10. A pump 11 is placed in the feed canal 9 for the transport of the culture medium. The pump 11 can be turned on and off by means of a control apparatus (not shown). The exit opening 5 of the micro-flow chamber 2, is joined by means of a connecting line 12, to an exhaust opening 13 for release of the culture medium. In the measuring space 3, the biocompartments 1 stand in contact with the culture medium.

In the base of the measuring space 3, are placed a plurality of ISFET's 14. As shown in FIG. 2, the ISFET's possess a substrate 15 comprised of semiconductor material, in which are placed highly doped zones with conducting lines printed remote from substrate 15 to connect the electronic drain 16 and source 17. Between drain 16 and source 17, is a gate 18. Gate 18, drain 16 and source 17 are electrically insulated from the measurement space 3 by means of a silicon nitride layer (not shown). The silicon nitride layer forms on its side remote from the gate 18, an active sensor layer. By means of which layer, the ISFET 14 is controllable through the hydrogen ions present in the culture medium. Gate 18, drain 16 and source 17 of the ISFET are connected with a known evaluation apparatus for the determination of the pH value of the culture medium which is somewhat proportional to measurement signal of the respective ISFET 14.

As is particularly well presented in FIG. 2, an electrode 19 is placed in close proximity to the gates 18. This electrode 19 is constructed of a noble metal, such as palladium and is in direct contact with the culture medium. In the case of the embodiment as shown in FIGS. 1, 2, the operational electrode 19 is placed on the silicon nitride layer encapsulating the drain 16, the source 17 and gate 18 and further, electrode 19 peripherally encompasses the gate 18.

A reference electrode 20 is paired with the operational electrode 19, which contacts the culture medium at a spatial distance from the ISFET 14. In the embodiment as shown in FIG. 1, this reference electrode 20 is placed in the outlet line 12 for the culture medium. The reference electrode 20 and the operational electrodes 19, can be connected to an electrical source of potential for the application of an electric potential on the culture medium.

By means of the above described measurement arrangement, the respiratory activities of the biocompartments 1 can be indirectly measured. To carry out this purpose, the pump 11, which acts to transport the through-put of the culture medium through the measurement space 3, is temporarily stopped. In FIG. 4, the period of time during which the through-put in the measurement space 3 is stopped, is designated as the time T1 (stopping the pump 11) and T2 (starting the pump 11). This time interval can run, for instance, some 8 minutes.

Subsequently, by means of the ISFET 14, a first $pH_{-1}$ is measured for the pH value of the culture medium, preparatory to a first pH measurement pair. Next, in a partial area of the culture area found in the active zone of the biocompartments 1, the electrical potential on the operational electrode 19, by the application of an electrical voltage between the reference electrode 20 and the operational electrode 19, drops so far into the negative area, that hydroxyl ions are formed from the oxygen found in the culture medium. When this occurs, this potential preferably is set at some −700 to −800 millivolts. In the embodiment of FIG. 3, this potential is applied to the electrodes 19, 20. The surface of the operational electrode 19 exposed to contact with the culture medium is chosen to be as small as possible with potential measuring preferably less than 1000 $\mu m^2$, so that, during the application of electrical voltage, the consumption of oxygen at the operational electrode 19 will be held at the lowest possible level.

In FIG. 4, the period of time, within which the negative potential is applied to the operational electrode 19, is designated with a double arrow Pf1. During the application of the negative electrical potential, the oxygen present in the zone of the operational electrode 19 is reduced in accord with the following reaction equations:

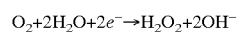

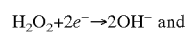

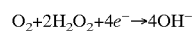

The hydroxyl ions generated in this way at the operational electrode 19 activate a localized pH change in the culture medium, which can be measured by means of the ISFET 14. In FIG. 4, one can quickly observe, that the pH value, during the application of the negative electrical potential on the operational electrode 19, increases in a degree corresponding to the oxygen content of the culture medium. Since the generated hydroxyl ions at the operational electrode 19 diffuse from the said operational electrode 19, and a forms a concentration gradient, the operational electrode 19 is placed as close as possible to the gate 18 of the ISFET, so that, upon the detection of these hydroxyl ions, the greatest possible sensitivity of the ISFET is achieved.

In the case of the negative potential in force on the operational electrode 19, by means of the ISFET 14, a second pH measured value, i.e. $pH_{-2}$ is determined in the culture medium for a first pH measurement pair. Subsequently, the electrical potential is raised to such a level, that the formation of hydroxyl ions from the oxygen carried in the culture medium is repressed. The level could be between zero and +800 millivolts. FIG. 4 plainly shows, that the pH value decreases with the recession of the potential lowering.

At this point, by means of the ISFET 14 there is determined a first measured $pH_{-3}$ to establish a second measured pH pair for the pH value of the culture medium, and subsequently, the potential on the operational electrode 19 is again lowered into the negative zone so far that hydroxyl ions are formed from the oxygen found in the culture medium. FIG. 4 clearly shows the corresponding increase of the measurement signal of the ISFET.

At this point, a second measured pH. i.e. $pH_{-4}$ is obtained by the ISFET for the second pH measured value pair and subsequently, the electrical potential is raised to the point, that the formation of hydroxyl ions from the oxygen in the culture medium is repressed. Furthermore, the pump 11 is again activated.

There is now obtained, from the chronologically proximal, mutually related, first and second pH measurement values of the two pH measurement pairs, a pH differential value expressed as:

$$\Delta pH_{-21} = pH_{-2} - pH_{-1}$$

$$\Delta pH_{-43} = pH_{-4} - pH_{-3}$$

This relationship presents a measurement for the oxygen content to be found in the culture medium. From the difference of, $(\Delta pH_{-43} - \Delta pH_{-21})$ these chronologically sequential difference values of $(pH_{-43} - pH_{-21})$ and the difference $\Delta T$ between the time values, on which the pH difference values $pH_{-41}$, $pH_{-21}$ were measured, provides the respiratory activity or breathing capacity of the biocompartments, which is expressed as:

$$\frac{\Delta pH_{-43} - \Delta pH_{-21}}{\Delta T}$$

Additionally, from the difference of the first measurement values $pH_{-1}$, $pH_{-3}$, the acidification, namely:

$$\Delta pH_{31} = pH_{-3} - pH_{-1}$$

is determined. In the embodiments provided in FIG. 4 to FIG. 6, this pH value is negative, that is, the biocompartments-acidification took place during a stand-still phase of the pump 11. In FIG. 5 and FIG. 6, this acidification was respectively indicated by a dotted straight line increment 21. The metabolism of the compartment 1 is now defined from the so achieved measurement values of respiratory activity and the acidification. For instance, in this way, the oxygen emission and generation of alkalinity for algae were measured.

The process steps arising from the lowering and raising of the electrical potential at the working electrode 19, as well as the obtaining of respectively first pH-measurement values $pH_{-1}$ and $pH_{-3}$ and respectively a second pH measurement value $pH_{-2}$ and $pH_{-4}$, can, in some cases, be repeated several times during the stand-still phase of the pump 11, as this is shown in the embodiment examples of FIG. 5 to FIG. 7. In FIG. 5 to FIG. 7, at the determined pH difference value repetition "i" of this procedure step, the designation $\Delta pH_{i+1,i}$ is applied.

In the embodiment in accordance with FIG. 5, the culture medium is essentially free from cell-affecting agents. During the stand-still phase of pump 11, marked as time points T1 and T2, an unmistakable acidification of the culture medium by the biocompartments 1 becomes evident. As may be seen from the difference of the pH differential values $\Delta pH_{-43}$ and $\Delta pH_{i+1,i}$, the biocompartments are consuming oxygen from the culture medium.

In the case of the embodiment in accordance with FIG. 6, the culture medium contains iodine acetate as a cell-affecting agent. By comparing this with FIG. 5, one sees that the acidification $\Delta pH_{-31}$, activated by the biocompartments 1, recedes. The iodine acetate hinders the biocompartments 1 in a forceful manner from releasing hydrogen ions to the culture medium. In comparison to FIG. 5, one notes that the iodine acetate causes an increase in the respiratory activity of the biocompartments 1.

Referring now to the embodiment example of FIG. 7, the culture medium contains the detergent Triton® which leads to the dying out of the biocompartments 1. Clearly it may be seen, that the biocompartments 1, after exposure to the Triton®, because of the dissolution of the mitochondrial chain, shows no further sign of respiratory activity and also biocompartments 1 no longer influence the culture medium.

FIGS. 5 to 7 show further, that the times for the measurement of the first and second pH measured values are coordinated with the times at which the electrical potential at the operational electrode is lowered or raised.

This fact results in a situation in which the rate of formation of the hydroxyl ions at the time of measurement corresponds, essentially, to the rate of formation of the hydroxyl ions at the time shortly before the lowering or the raising of the electrical potential. The hydroxyl ion concentration finds itself, on this account, in a dynamic equilibrium. In FIG. 5 to FIG. 7, are some of the first and second pH measurements respectively marked by horizontal, dotted lines.

In the embodiment in accord with FIG. 8, following the shutting off of the pump 11, there is initially measured a first measurement $pH_{-1}$ and a second measurement $pH_{-2}$ to form a first pH measurement pair of a nitrogen monoxide concentration, wherein the procedure is then carried out in accord with the embodiment example shown in FIG. 3. Thereafter, the electrical potential is shut off. Subsequently, by means of the ISFET 14, measurements are made for a first measurement value $pH_{+1}$ for a first pH measurement pair of a nitrogen monoxide concentration measurement. Since the nitrogen monoxide formed in the culture medium from the biocompartments 1, exhibits only a small half-life, the ISFET 14 is advantageously placed directly on the cell membrane or very close thereto. Then, in that portion of the culture medium found in the activity zone of the biocompartments 1, the electrical potential is raised to such a high level by means of applying an electrical voltage between the reference electrode 20 and the operational electrode 19, that the nitrogen monoxide found in the culture medium is employed to generate hydrogen ions. When this is done, this potential measures preferably ca. +700 to +800 millivolts, in relation to the potential of the reference electrode 20. Then, by means of ISFET 14 a second pH-measurement value, namely $pH_{+2}$ for the first pH measured value pair of the nitrogen monoxide concentration measurement in the culture medium is determined.

In FIG. 8, the time intervals, in which the positive electrical potential is applied on the electrodes 19, 20, are designated by the double arrow Pf1. The time intervals in which the negative electrical potential is applied on the electrodes 19, 20 are designated by the double arrow Pf2. During the application of the positive electrical potentials, in the area of the operational electrode 19, the nitrogen monoxide found in the culture medium is reduced in accordance with the reaction equation:

$$NO + H_2O - e^- \rightarrow NO_2 + 2H^+$$

Since, as this occurs, the hydrogen ions formed on the operational electrode 19, so act as to form within the culture medium, a local change of the pH value, which can be measured by means of the ISFET 14. In FIG. 8, readily seen, is that the pH value during the application of the positive electrical potential on the operational electrode 19 decays about an amount corresponding to the nitrogen monoxide content of the culture medium.

At this point the electrical potential is shut off again, and a first measured value $pH_{-3}$ is established for a second pH measurement value pair of the oxygen concentration determination. Subsequently, the potential at the operational electrode 19 is dropped so far into the negative range, that from the oxygen found in the culture medium, hydroxyl ions are produced. Now a second pH measured value, namely $pH_{-4}$ of the second pH measured value pairs of the oxygen concentration is obtained by means of the ISFET 14. After this, the electrical potential is shut off, and a first measured value $pH_{-3}$ for a second pH measurement pair of the nitrogen monoxide measurement is obtained. Subsequent to this, the electric potential is once again increased to such a level, that from the nitrogen monoxide found in the culture medium, hydrogen ions are formed. At the same time, a second pH measurement value, $pH_{+4}$ of the second pH measurement value pair is obtained of the nitrogen monoxide concentration measurement by means of the ISFET 14, and the pump 11 is once again turned on.

From the pH differences:

$$\Delta pH_{-21} = pH_{-2} - pH_{-1}$$

$$\Delta pH_{-43} = pH_{-4} - pH_{-3}$$

the respiratory activity for the biocompartments can be calculated in a similar manner to the embodiment of FIG. 4, i.e. by $$\frac{\Delta pH_{-43} - \Delta pH_{-21}}{\Delta T}$$

Further, from the pH difference values:

$$\Delta pH_{+21} = pH_{+2} - pH_{+1}$$

$$\Delta pH_{+43} = pH_{+4} - pH_{+3}$$

the concentration change of the nitrogen monoxide, namely:

$$\frac{\Delta pH_{+43} - \Delta pH_{+21}}{\Delta T}$$

can be determined in the culture medium.

Also, measurement values:

$$\Delta pH_{-31} = pH_{-3} - pH_{-1}$$

$$\Delta pH_{+31} = pH_{+3} - pH_{+1}$$

formed for the acidification.

In a corresponding manner, in the case of biocompartments 1, which, in the course of metabolism, can either consume or release hydrogen peroxide ($H_2O_2$), these products can be measured by means of the concentration change of the hydrogen peroxide produced by the said biocompartments 1. As part of the procedure, during the application of the positive electrical potential in the immediate neighborhood of the operational electrode 19, the hydrogen peroxide found in the culture medium is reduced in accordance with the following equation:

$$H_2O_2 - 2e^- \rightarrow O_2 + 2H^+$$

Mention should be made of the fact that the time span, during which the electrical potential is applied to the electrodes 19, 20 can be so apportioned, that the biocompartments 1 placed in proximity to the operational electrode 19 can be affected by the locally changed pH value caused by the electrical potential in the area of the operational electrode 19. Thereby, it becomes possible, for example, to investigate the influence of pH value on the effectiveness of a cell agent found in the culture medium.

Where the procedure for the investigation of biological biocompartments 1 is concerned, the measurement space of the micro-flow chamber containing the biocompartments 1 is continually or intermittently exposed to flowing culture medium.

In a culture medium portion neighboring the biocompartments 1, an electrical potential is applied in such a manner, that from a substance released by or absorbed from biocompartments in the culture medium, $OH^-$ and/or $H^+$ ions are formed. During the application of the potential, a first measurement value $pH_{-1}$, $pH_{-3}$, $pH_{+1}$, $pH_{+3}$ is measured for the pH value of the culture medium. Then the potential is switched off, or changed in such a manner, that the formation of $OH^-$ and/or $H^+$ ions in the substance is stopped. Before or after the measurement of the first measured value $pH_{-1}$, $pH_{-3}$, $pH_{+1}$, $pH_{+3}$, and upon switched off electrical potential, or with a potential at which the formation of hydroxyl and hydrogen ions from the material is repressed, a second measurement value $pH_{-2}$, $pH_{-4}$, $pH_{+2}$, $pH_{+4}$ is determined for the pH value of the culture medium. After the entire measurement has been repeated at least once, from the first and the second measurement values, the concentration change of the material in the culture medium and the acidification or alkalinization of the culture medium is determined.

What is claimed is:

1. A process for examining membrane enclosed biocompartments (1), wherein the biocompartments (1) are arranged in a micro-flow chamber (2) which includes an o rational electrode 19 for placing the biocompartments (1) in proximity thereto and a reference electrode (20) separated from the operational electrode (19); the micro-flow chamber (2) is subject to through-flow of a culture medium containing an agent which can affect the biocompartments (1), the medium being in contact with the biocompartments (1) whereby a concentration of a substance is released by and/or consumed by metabolic action into and/or from a portion of a culture medium contained in an activity area of the biocompartment (1), and wherein the pH value of that portion of the culture medium which is found within the micro-flow chamber (2) is measured to determine a metabolic activity of the biocompartment, the process comprising:

a) applying a voltage to the culture medium (1) so that hydroxyl ions or hydrogen ions are formed from the substance in the culture medium;

b) at a measuring location in the portion of the culture medium, prior to or during the application of the voltage, measuring at least a first measurement value ($pH_{-1}$, $PH_{-3}$ or $pH_{+1}$, $pH_{+3}$) for a pH value of the culture medium;

c) subsequently switching off or changing the voltage so that the formation of hydroxyl and hydrogen ions from the substance is stopped;

d) before or after measurement of the first measurement value, ($pH_{-1}$, $pH_{-3}$ or $pH_{+1}$, $pH_{+3}$), upon switching off or changing the voltage such that the formation of hydroxyl and hydrogen ions from the substance is repressed, taking at least one second measurement value ($pH_{-2}$, $pH_{-4}$ or $pH_{+2}$, $pH_{30\ 4}$) for the pH value of the culture medium;

e) calculating a difference between the first measurement value ($pH_{-1}$, $pH_{-3}$ or $pH_{+1}$, $pH_{+3}$) and the second measurement value ($pH_{-2}$, $pH_{-4}$ or $pH_{+2}$, $pH_{+4}$), to produce a measurement value difference ($\Delta pH_{-21}$, $\Delta pH_{-43}$ or $\Delta pH_{-21}$, $\Delta pH_{-43}$);

f) repeating the steps a) to e) at least once;

g) calculating a difference between at least two of the meaeu*ed measurement value differences ($\Delta pH_{-21}$, $\Delta pH_{-43}$ or $\Delta pH_{+21}$, $\Delta pH_{+43}$) to determine a concentration change of the substance in the culture medium; and calculating a difference between at least two of the first measurement pH values ($pH_{-1}$, $pH_{-3}$ or $pH_{+1}$, $p_{+3}$) and/or calculating a difference between at least two of the second measurement values ($pH_{-2}$, $pH_{-4}$ or $pH_{+2}$, $pH_{+4}$) to determine the an acidification or alkalinization of the culture medium; and h) from the measurement values for the concentration change and the acidification or the alkalinization, determining the metabolic activity of the biocompartments (1).

2. A process in accordance with claim 1, wherein the sequence comprised of the steps a) to g) is run through at least twice, and that in accordance with this repetition, the electrical polarity applied between the operational electrode (19) and the reference electrode (20) is selected on a changeable basis.

3. A process in accordance with claim 1, wherein a time for the measurement of the measurement values ($pH_{-1}$, $pH_{-2}$, $pH_{-3}$, $pH_{-4}$, or $pH_{+1}$, $pH_{+2}$, $pH_{+2}$, $pH_{+4}$) is adjusted to coincide with a time at which the voltage is changed or switched off, and the hydrogen ion and hydroxy ion concentrations in the culture medium are generally in balance.

4. A process in accordance with claim 1, wherein a time interval between the respective times of the application, the switching off or change in the voltage, and a subsequent time in which the measurement value ($pH_{-1}$, $pH_{-2}$, $pH_{-3}$, $pH_{-4}$, or $pH_{+1}$, $pH_{+2}$ $pH_{+3}$, $pH_{+4}$) is measured, are approximately the same at all pH measurement values ($pH_{-1}$, $pH_{-2}$, $pH_{-3}$, $pH_{-4}$, or $pH_{+1}$, $pH_{+2}$ $pH_{+3}$, $pH_{+4}$.

5. A process in accordance with claim 1, wherein the voltage is switched off, or, in accordance with Step c, is changed, before an equilibrium state of the hydrogen and hydroxyl ion concentrations has established itself in the culture medium.

6. A process in accordance with claim 1, further comprising measuring the flowing electric electrode current between the operational electrode (19) and the reference electrode (20).

7. A process in accordance with claim 1, wherein the biocompartments (1) are installed in such a manner on the operational electrode (19), that, area-wise, they partially cover the electrode (19) and that from the applied voltage between the operational electrode (19) and the reference electrode (20) on the electrode current, the morphology of the biocompartments (1) can be determined.

8. A process in accordance with claim 1, wherein the through-flow of the culture medium is halted or at least reduced during and between the times of acquiring of the first and last pH measurement values of the a measured pH value series for a determination of a concentration change of the substance in the culture medium and the acidification or the alkalinization thereof.

9. A process in accordance with claim 1, wherein between the determination of the first and last pH measurement values of a pH value series of measurements, the buffer capacity of the culture medium is held constant.

10. A process for examining membrane enclosed biocompartments (1), wherein the biocompartments (1) are arranged in a chamber which includes an operational electrode (19) for placing the biocompartments (1) in proximity thereto and a reference electrode (20) separated from the operational electrode (19); the chamber is subject to through-flow of a culture medium containing an agent which can affect the biocompartments (1), the medium being in contact with the biocompartments (1) whereby a concentration of a substance is released by and/or consumed by metabolic action into and/or from a portion of a culture medium contained in an activity area of the biocompartment (1), and wherein the pH value of that portion of the culture medium which is found within the chamber (2) is measured to determine a metabolic activity of the biocompartment, the process comprising:

a) applying a voltage to the culture medium (1) so that hydroxyl ions or hydrogen ions are formed from the substance in the culture medium;

b) at a measuring location in the portion of the culture medium, during the application of the voltage, measuring at least a first measurement value ($pH_{-1}$, $pH_{-3}$ or $pH_{+1}$, $pH_{+3}$) for a pH value of the culture medium;

c) subsequently switching off or changing the voltage so that the formation of hydroxyl and hydrogen ions from the substance is stopped;

d) before or after measurement of the first measurement value ($pH_{-1}$, $pH_{-3}$ or $pH_{+1}$, $pH_{+3}$), upon switching off or changing the voltage such that the formation of hydroxyl and hydrogen ions from the substance is repressed, taking at least one second measurement value ($pH_{-2}$, $pH_{-4}$ or $pH_{+2}$, $pH_{+4}$) for the pH value of the culture medium;

e) calculating a difference between the first measurement value ($pH_{-1}$, $pH_{-3}$ or $pH_{+1}$, $pH_{+3}$) and the second measurement value ($pH_{-2}$, $pH_{-4}$ or $PH_{+2}$, $pH_{+4}$, to produce a measurement value difference ($\Delta pH_{-21}$, $\Delta pH_{-43}$ or $\Delta pH_{+21}$, $\Delta pH_{+43}$);

f) repeating the steps a) to e) at least once;

g) calculating a difference between at least two of the measurement value differences ($\Delta pH_{-21}$, $\Delta pH_{-43}$ or $\Delta pH_{+21}$, $\Delta pH_{+43}$) to determine a concentration change of the substance in the culture medium; and calculating a difference between at least two of the first measurement values ($pH_{-1}$, $pH_{-3}$ or $pH_{+1}$, $pH_{+3}$) and/or calculating a difference between at least two of the second measurement values ($pH_{-2}$, $pH_{-4}$ or $pH_{+2}$, $pH_{+4}$) to determine an acidification or alkalinization of the culture medium; and h) from the measurement values for the concentration change and the acidification or the alkalinization, determining the metabolic activity of the biocompartments (1).

* * * * *